US010987501B2

(12) United States Patent
Hwang et al.

(10) Patent No.: US 10,987,501 B2
(45) Date of Patent: *Apr. 27, 2021

(54) CELL IMPREGNATED SLEEVE FOR PARACRINE AND OTHER FACTOR PRODUCTION

(71) Applicant: The Johns Hopkins University, Baltimore, MD (US)

(72) Inventors: Chao-Wei Hwang, West Friendship, MD (US); Zhiyong Xia, Rockville, MD (US); Virginia E. Bogdan, Owings Mills, MD (US); Jeffrey A. Brinker, Baltimore, MD (US); Gary Gerstenblith, Reisterstown, MD (US); Peter V. Johnston, Baltimore, MD (US); Steven P. Schulman, Baltimore, MD (US); Gordon Tomaselli, Baltimore, MD (US); Robert G. Weiss, Cockeysville, MD (US)

(73) Assignee: The Johns Hopkins University, Baltimore, MD (US)

( * ) Notice: Subject to any disclaimer, the term of this patent is extended or adjusted under 35 U.S.C. 154(b) by 24 days.

This patent is subject to a terminal disclaimer.

(21) Appl. No.: 16/728,079

(22) Filed: Dec. 27, 2019

(65) Prior Publication Data

US 2020/0147358 A1    May 14, 2020

Related U.S. Application Data

(62) Division of application No. 15/025,902, filed as application No. PCT/US2014/059400 on Oct. 7, 2014, now Pat. No. 10,561,830.

(60) Provisional application No. 61/896,821, filed on Oct. 29, 2013, provisional application No. 61/888,073, filed on Oct. 8, 2013.

(51) Int. Cl.
| *A61M 37/00* | (2006.01) |
| *A61M 25/10* | (2013.01) |
| *A61L 33/00* | (2006.01) |
| *A61L 27/18* | (2006.01) |
| *A61L 27/38* | (2006.01) |
| *A61L 27/54* | (2006.01) |
| *A61L 27/56* | (2006.01) |
| *A61L 31/00* | (2006.01) |
| *A61L 31/14* | (2006.01) |
| *A61L 31/16* | (2006.01) |
| *A61L 31/06* | (2006.01) |
| *A61F 2/04* | (2013.01) |
| *A61L 31/10* | (2006.01) |
| *A61L 33/08* | (2006.01) |
| *A61F 2/07* | (2013.01) |

(52) U.S. Cl.
CPC ............... *A61M 37/00* (2013.01); *A61F 2/04* (2013.01); *A61L 27/18* (2013.01); *A61L 27/3834* (2013.01); *A61L 27/54* (2013.01); *A61L 27/56* (2013.01); *A61L 31/005* (2013.01); *A61L 31/06* (2013.01); *A61L 31/10* (2013.01); *A61L 31/14* (2013.01); *A61L 31/146* (2013.01); *A61L 31/16* (2013.01); *A61L 33/0011* (2013.01); *A61L 33/08* (2013.01); *A61F 2002/072* (2013.01); *A61L 2300/252* (2013.01); *A61L 2300/256* (2013.01); *A61L 2300/42* (2013.01); *A61L 2300/64* (2013.01); *A61L 2400/12* (2013.01); *A61L 2400/18* (2013.01); *A61L 2420/02* (2013.01); *A61M 2202/09* (2013.01); *A61M 2205/04* (2013.01)

(58) Field of Classification Search
CPC ...... C08L 67/04; A61L 2300/42; A61L 27/18; A61L 31/10; A61L 31/146; A61L 27/3834; A61L 2420/02; A61L 2300/252; A61L 2300/64; A61L 31/06; A61L 33/0011; A61L 2400/18; A61L 31/14; A61L 2400/12; A61L 33/08; A61L 31/005; A61L 27/56; A61L 27/54; A61L 31/16; A61L 2300/256; A61F 2/04; A61F 2002/072; A61M 2202/09; A61M 37/00; A61M 2205/04

See application file for complete search history.

(56) References Cited

U.S. PATENT DOCUMENTS

| 7,972,616 | B2 | 7/2011 | Dubrow et al. |
| 8,303,972 | B2 | 11/2012 | Michal |
| 8,403,980 | B2 | 3/2013 | Wachter et al. |
| 8,518,431 | B2 | 8/2013 | Spedden et al. |
| 2007/0041952 | A1 | 2/2007 | Guilak et al. |
| 2007/0269481 | A1 | 11/2007 | Li et al. |
| 2008/0077222 | A1 | 3/2008 | Johnson et al. |
| 2008/0083617 | A1 | 4/2008 | Simpson et al. |
| 2009/0018643 | A1 | 1/2009 | Hashi et al. |

(Continued)

FOREIGN PATENT DOCUMENTS

WO    2006/069349    6/2006

OTHER PUBLICATIONS

Kolambkar, Yash M., "Electrospun Nanofiber Meshes for the Functional Repair of Bone Defects," Dissertation, Georgia Institute of Technology, Dec. 2009, pp. 1-216.

(Continued)

*Primary Examiner* — Satyendra K Singh
(74) *Attorney, Agent, or Firm* — Noah J. Hayward

(57) ABSTRACT

Certain embodiments according to the present invention provide sleeve devices suitable for a wide range of therapeutic uses. In accordance with certain embodiments, the therapeutic sleeve device includes a nanofiber fabric assembly, which defines a plurality of pores, and at least one layer of cells embedded in the nanofiber fabric assembly.

17 Claims, 7 Drawing Sheets

(56) References Cited

U.S. PATENT DOCUMENTS

| | | |
|---|---|---|
| 2009/0091065 A1 | 4/2009 | Katti et al. |
| 2010/0233234 A1 | 9/2010 | Arinzeh et al. |
| 2011/0229551 A1 | 9/2011 | Doshi et al. |
| 2011/0230411 A1 | 9/2011 | Zussman et al. |
| 2011/0268776 A1 | 11/2011 | Schapira et al. |
| 2011/0280912 A1 | 11/2011 | Langer et al. |
| 2012/0083767 A1 | 4/2012 | Gerstenblith et al. |
| 2013/0138155 A1 | 5/2013 | Hoornaert et al. |
| 2013/0172988 A1 | 7/2013 | Kutryk et al. |
| 2015/0335788 A1 | 11/2015 | Xia et al. |

OTHER PUBLICATIONS

WIPO, Written Opinion of the International Searching Authority, PCT/US2014/059400, dated Jan. 16, 2015, pp. 1-4.

WIPO, International Search Report, PCT/US2014/059400, dated Jan. 16, 2015, pp. 1-2.

F. Duttenhoefer, et al., "3D Scaffolds Co-Seeded \vith Human Endothelial Progenitor and Mesenchymal Stem Cells: Evidence of Prevascularisation '\vithin 7 Days," European Cells and Materials, pp. 49-65, 2013.

Thermofischer, "Useful Nos. For Cell Culture," pp. 1-2, downloaded Aug. 5, 2019.

Nagaya N., et al., "Transplantation of Mesenchymal Stem Cells Improves Cardiac Function in a Rat Model of Dilated Cardiomyopathy", Circulation, 2005, vol. 112, pp. 1128-1135, (Year: 2005).

Li Wan-Ju., et al., "Fabrication and Application of Nanofibrous Scaffolds in Tissue Engineering", Curr Protoc. Cell Biol., Author manuscript; available in PMC 2010, Jan. 18, pp. 1-15, (Year: 2010).

Kam P. C. A., et al., "Platelet Glycoprotein lib/llla Antagonists, Pharmacology and Clinical Developments", Anesthesiology, 2002; vol. 96, pp. 1237-1249, (Year: 2002).

Satori C.P., et al., "Bioanalysis of eukaryotic organelles", Chem. Rev., Apr. 10, 2013, vol. 113, No. 4, pp. 2733-2811, attached as Author Manuscript available in PMC, total pp. 1-163 (Year: 2013).

CELL IMPREGNATED SLEEVE FOR PARACRINE AND OTHER FACTOR PRODUCTION

CROSS-REFERENCE TO RELATED APPLICATIONS

This application is divisional of prior-filed, co-pending U.S. Nonprovisional application Ser. No. 15/025,902, which has a 371 national stage acceptance date of Mar. 30, 2016 and is based on prior-filed International Application No. PCT/US14/59400, filed on Oct. 7, 2014, which claims priority to and the benefit of prior-filed U.S. Provisional Application Ser. Nos. 61/896,821 and 61/888,073, filed on Oct. 29, 2013 and Oct. 8, 2013, respectively, the contents of all of which are herein incorporated by reference in their entireties.

TECHNICAL FIELD

The presently-disclosed invention relates generally to fibrous non-woven sleeve devices, and more particularly to a cell-impregnated fibrous non-woven sleeve device that may provide a platform for paracrine factor production in the body. According to certain embodiments, the non-woven sleeve device forms a "cage" for cells to produce paracrine factors without cell dilution, washout, and immune attack.

BACKGROUND

Heart failure afflicts more than 6 million Americans. Despite advances in heart failure therapy, there is no clinically available intervention to reverse underlying heart muscle injury. In recent years, stem cell therapy has been proposed as a way to regenerate the damaged tissue. It has become clear that stem cells' capacity to heal derives in large part from their ability to produce growth factors that accelerate the body's own repair mechanisms. However, current methods to administer stem cells to the heart, including intracoronary infusion or direct intramyocardial injection, are not conducive to the sustained production of beneficial growth factors. Rapid cell dilution, washout, and immune attack limit retention of viable stem cells, and, consequently, diminish the ability of the stem cells to produce sufficient growth factors to have desirable clinical effects.

BRIEF SUMMARY

Certain embodiments according to the present invention provide sleeve devices suitable for a wide range of therapeutic uses. In accordance with certain embodiments, the therapeutic sleeve device includes a nonwoven fiber fabric assembly, which defines a plurality of pores, and a plurality of cells embedded in the nonwoven fiber fabric assembly.

In accordance with certain embodiments, there is a method of treatment to heal damaged tissue. To heal damaged tissue, the therapeutic sleeve device can be prepared and wrapped around an object. By wrapping the therapeutic sleeve device around an object, the cells embedded in the therapeutic sleeve device can produce paracrine factors without being subject to dilution, washout, or attack from the immune system of the subject.

BRIEF DESCRIPTION OF THE DRAWING(S)

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

DETAILED DESCRIPTION

Figure 1:
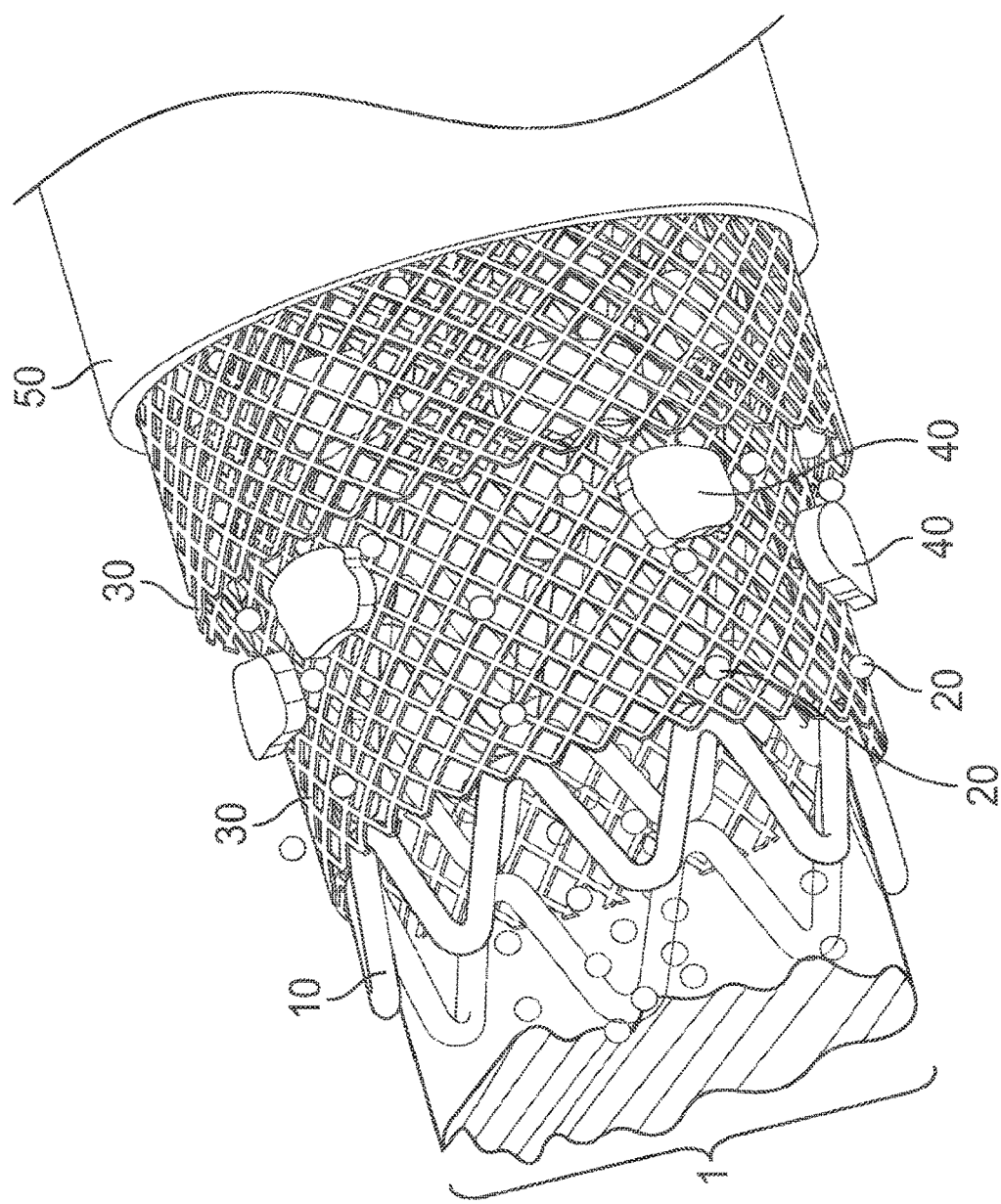
FIG. 1 illustrates a schematic overview of the therapeutic sleeve device according to certain embodiments of the present invention.

The present invention now will be described more fully hereinafter with reference to the accompanying drawings, in which some, but not all embodiments of the inventions are shown. Indeed, this invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present invention includes a nonwoven fiber fabric assembly with embedded cells (e.g., stem cells) wrapped around a medical instrument, which provides a platform from which stem cells can be placed so that they can release factors to injured tissue, while also being shielded from dilution, washout, and immune attack, in order to provide continuous production of pro-healing paracrine factors. As such, for example, the platform may be placed directly at or near the site of the injured tissue, or may be placed remotely from the injured tissue so long as the factors are enabled to communicate with the injured tissue.

Although nanofiber fabric assemblies are frequently referenced throughout this disclosure, nanofiber fabric assemblies serve only as an example of a nonwoven fiber fabric assembly that may be used to form the therapeutic sleeve device. Moreover, although stem cells are frequently referenced throughout this disclosure, stem cells serve only as an exemplary application of the present invention, which could be applicable to a wide variety of cell-based therapies. Additionally, although growth factors are frequently referenced throughout this disclosure, growth factors serve only as an example of a constituent of the secretome produced by cells embedded in the nanofiber fabric assembly. Furthermore, although stents are frequently referenced as an application of the therapeutic sleeve device throughout this disclosure, stents serve only as an exemplary application of the present invention, which could be applicable to a wide variety of medical instruments.

As used herein, the term "layer" may comprise a region of a given material whose thickness is small compared to both its length and width. As used herein a layer need not be planar, for example, taking on the contours of an underlying substrate. A layer can be discontinuous (e.g., patterned). Terms such as "film," "layer" and "coating" may be used interchangeably herein.

The term "nonwoven", as used herein, may comprise a web having a structure of individual fibers or threads which are interlaid, but not in an identifiable manner as in a knitted or woven fabric. Nonwoven fabrics or webs have been formed by many processes such as, for example, meltblowing processes, spunbonding processes, hydroentangling, airlaid, and bonded carded web processes.

The term "nanofiber fabric layer", as used herein, may comprise a layer of nanofibers processed to form a fabric. The term "nanofiber", as used herein, may comprise a nonwoven fiber having a thickness from about 1 nanometer to about 999 nanometers. As used herein, a nanofiber may comprise any sub-micron fiber. The nanofiber fabric layer may comprise a synthetic biocompatible material, a biological material, or any combination thereof. Synthetic biocompatible materials may comprise bioabsorbable materials. Synthetic biocompatible materials may comprise poly(lactic acid) ("PLA"), poly(L-lactic acid) ("PLLA"), poly(lactic-co-glycolic acid) copolymer ("PLGA"), polycaprolactone ("PCL"), or polyethylene terephthalate ("PET"). Biological materials may comprise collagen, peptides, proteins, nucleic acids, fatty acids, gelatin, chitosan, or hyaluronic acid.

The term "pore", as used herein, may comprise any structure formed by the nonwoven fiber fabric assembly having a maximal pore size. The random arrangement of the nonwoven fibers may create irregular pore structures. Thus, the pores may have irregular shapes and inconsistent sizes generally. As such, the maximal pore size should be understood to correlate to the size of the smallest object that would be retained by or prevented from passing through the pore. Meanwhile, average pore size may correspond to an average value for all of the maximal pore sizes in the assembly.

The term "tissue", as used herein, may comprise any component of the body, including, but not limited to, muscle, blood vessels, bone, fat tissue, or skin.

The term "paracrine factor", as used herein, may comprise one or more members of the entire secretome of a cell. As used herein, paracrine factors may act locally or systemically. Paracrine factors may comprise growth factors, nucleic acids (e.g., micro-RNA), or extracellular vesicles (e.g., exosomes).

The term "stem cell", as used herein, may comprise hematopoietic or non-hematopoietic cells which exist in almost all tissues and have the capacity of self-renewal and the potential to differentiate into multiple cell types. Tissue injury is associated with the activation of immune/inflammatory cells, not only macrophages and neutrophils but also adaptive immune cells (e.g., $CD4^+$ T cells, $CD8^+$ T cells, B cells), which are recruited by factors from, for example, apoptotic cells, necrotic cells, damaged microvasculature and stroma. Meanwhile, inflammatory mediators (e.g., TNF-$\alpha$, IL-1$\beta$ free radicals, chemokines, leukotrienes) are often produced by phagocytes in response to damaged cells and spilled cell contents. Thus, these inflammatory molecules and immune cells, together with endothelial cells and fibroblasts, orchestrate changes in the microenvironment that result in the mobilization and differentiation of stem cells into stroma and/or replacement of damaged tissue cells. Once stem cells have entered the microenvironment of injured tissues, for example, many factors (e.g., cytokines such as TNF-$\alpha$, IL-1, IFN-$\gamma$, toxins of infectious agents and hypoxia) can stimulate the release of many factors from the stem cell secretome (e.g., epidermal growth factor (EGF), fibroblast growth factor (FGF), platelet-derived growth factor (PDGF), transforming growth factor-$\beta$ (TGF-$\beta$), vascular endothelial growth factor (VEGF), hepatocyte growth factor (HGF), insulin growth factor-1 (IGF-1), angiopoietin-1 (Ang-1), keratinocyte growth factor (KGF), stromal cell-derived factor-1 (SDF-1)). These growth factors, in turn, promote tissue regeneration and repair (Ma et al. (2014) *Cell Death and Differentiation* (2014) 21, 216-225).

The term "embedded", as used herein, may generally refer to the placement and capture of cells within nanofiber fabric either secured between nanofiber fabric layers, within nanofiber fabric layers, or on the surface of a nanofiber fabric layer.

The term "adhesion molecule", as used herein, may comprise proteins which are expressed on the surfaces of a variety of cell types and which mediate cell-cell interactions and subsequent cellular and biological responses, including, but not limited to, T cell activation, leukocyte transmigration, and inflammation. Adhesion molecules may comprise fibronectin, fibrinogen, laminins, collagen, vitronectin, proteoglycans, aginyl-glycyl-aspartic (RGD) acid peptides, and/or cell specific antibodies (e.g., anti-CD29 antibody).

The terms "pre-incubation embedding", "post-incubation embedding", and "in-situ embedding", as used herein, may comprise methods of embedding cells in nanofiber fabric layers. Pre-incubation embedding may comprise culturing cells in standard tissue culture flasks using standard methods, harvesting the cells once confluent, re-concentrating the cells in media, immersing an unattached flat nanofiber sleeve in the concentrated cell suspension, incubating the nanofiber sleeve in the cell suspension to allow cell adhesion, and optionally adding adhesion molecules to improve the efficiency of cell incorporation into the nanofiber sleeve. Post-incubation embedding may comprise immersing a nanofiber sleeve attached to a medical device in a concentrated suspension of cells, placing the nanofiber sleeve attached to the medical device in a tissue culture incubator, optionally rotating it at regular intervals to promote uniform adhesion, and optionally adding adhesion molecules to improve the efficiency of cell incorporation into the nanofiber sleeve. In-situ embedding may comprise dripping, nebulizing, or microspraying cells directly onto a rotating stent or, alternatively, partially immersing a rotating stent in a continually agitated concentrated cell suspension. Adhesion molecules can optionally be added to improve the efficiency of cell incorporation into the nanofiber sleeve.

The term "host foreign cell", as used herein, may comprise any cells originating from the subject in whom the therapeutic sleeve device is inserted, which may comprise any subject immune cells.

The term "antithrombotic material", as used herein, may comprise any material (e.g. anticoagulants, anti-platelet agents) having utility in a variety of therapeutic areas including the prevention and/or treatment of arterial thrombosis, stent thrombosis, deep vein thrombosis (DVT) after surgery, major medical illness, paralysis, malignancy, prolonged immobilization trauma, application of lower limb plaster casts, or fractures of the lower limbs or pelvis; recurrent DVT; DVT during pregnancy when there is a previous history thereof; reocclusion following thrombolytic therapy; chronic arterial obstruction; peripheral vascular disease; acute myocardial infarction; unstable angina; atrial fibrillation; thrombotic stroke; transient ischaemic attacks; disseminated intravascular coagulation; coagulation in extra-corporeal circuits; occlusion of arterio-venous shunts and blood vessel grafts (including coronary artery by-pass grafts); and restenosis and occlusion following angioplasty.

The term "anticoagulant", as used herein, may comprise any agent that is used to prevent the formation of blood clots. Anticoagulants have various uses. Some are used for the prevention or treatment of disorders characterized by abnormal blood clots and emboli. Anticoagulant drugs include intravenous heparin, which acts by inactivating thrombin and several other clotting factors that are required for a clot to form, and oral anticoagulants such as warfarin and dicumarol, which act by inhibiting the liver's production of vitamin K-dependent factors that are crucial to clotting. Anticoagulants may comprise at least one of heparin, enoxaparin, apixaban, acenocoumarol, fondaparinux, bemiparin, bivalirudin, dalteparin, epoprostenol, tinzaparin, menadiol sodium phosphate, danaparoid, dabigatran etexilate mesilate, rivaroxaban, or warfarin.

The term "anti-platelet agent", as used herein, may comprise any agent that decreases platelet aggregation and inhibits thrombus formation. Anti-platelet agents may comprise at least one of irreversible cyclooxygenase inhibitors (e.g., acetylsalicylic acid, triflusal), adenosine diphosphate (ADP) receptor inhibitors (e.g., clopidogrel, prasugrel, ticagrelor, ticlopidine), phosphodiesterase inhibitors (e.g., cilostazol), protease-activated receptor-1 (PAR-1) antagonists (e.g., vorapaxar), glycoprotein IIB/IIIA inhibitors (e.g., abciximab, eptifibatide, tirofiban), adenosine reuptake inhibitors (e.g., dipyridamole), thromboxane synthase inhibitors (e.g., picotamide, naproxen), or thromboxane receptor antagonists (e.g., terutroban).

The term "agent-releasing material", as used herein, may comprise any material capable of releasing beneficial agents in the body. Such beneficial agents may comprise at least one of drugs, proteins, growth factors, extracellular vesicles such as exosomes, nucleic acids such as micro-RNA, cell nutrients, anticoagulants, anti-platelet agents, or anti-inflammatory agents.

The term "medical instrument", as used herein, may comprise any medical device to be used in conjunction with a therapeutic sleeve device. Medical instruments may comprise stents, pacemakers, vascular grafts, implantable cardioverter-defibrillators, pacemaker leads, implantable cardioverter-defibrillator leads, biventricular implantable cardioverter-defibrillator leads, artificial hearts, artificial valves, ventricular assist devices, balloon pumps, catheters, central venous lines, orthopedic implants, wound healing packing, or wound healing gauze.

The terms "direct electrospinning", "microsuturing", and "stent sandwiching", as used herein, may comprise methods of attaching a therapeutic sleeve device to a medical instrument. Direct electrospinning, for example, may comprise mounting a medical instrument (e.g., a stent) along the axis of a shaft rotating at approximately 100 rpm, placing a wire connected to a power source inside the lumen of an expanded stent or inside an unexpanded stent delivery balloon, loading nanofiber material (e.g., PLGA) at a concentration of 7.5 wt % in dichloromethane solvent, and drawing out the nanofiber material by a voltage potential onto the stent through an 18G blunt-tipped needle connected to a power source. Microsuturing may comprise attaching a therapeutic sleeve device to the inner, outer, or both aspects of a medical instrument (e.g., a stent) either entirely or partially, and crimping the therapeutic sleeve device-covered stent onto a delivery balloon prior to implantation. Stent sandwiching may comprise physically securing or leaving unattached one therapeutic sleeve device and one medical instrument (e.g., a stent), and crimping a second stent around the first stent so as to sandwich either completely or partially the therapeutic sleeve device between the two stents.

In one aspect, the present invention provides therapeutic sleeve devices suitable for a wide variety of end-uses. Therapeutic sleeve devices, according to certain embodiments of the present invention, may include many desirable features for delivering stem cell-based therapies, such as tailored local growth factor release, prevention of cell dilution and washout, and protection from immune attack to name just a few. In general, therapeutic sleeve devices according to certain embodiments of the present invention may be constructed of at least one layer of nanofiber fabric and at least one layer of cells embedded between the nanofiber fabric layer(s), within the nanofiber fabric layer(s), or on top of the nanofiber fabric layer(s).

In accordance with certain embodiments of the present invention, the nanofiber fabric defines a plurality of pores. The pores are configured to have a maximal pore size less than the embedded cell diameter. Thus, the pores in the nanofiber fabric layer(s) act as a "cage" for the embedded cells, thereby preventing cell dilution and washout. The pores are further configured to have a maximal pore size less than other cell diameters. In this regard, the maximal pore size is less than any immune cell diameter, thereby protecting the embedded cells from immune attack. The pores are further configured to have a maximal pore size greater than any paracrine factors, nutrients required by the embedded cells, and any wastes or cellular products produced by the embedded cells. In this regard, the maximal pore size accommodates the needs of the cells embedded therein. In this regard, certain embodiments of the present invention may comprise protection against immune attack, dilution, and cell washout while further providing a beneficial environment for the embedded cell health.

The nanofiber fabric layer(s), according to certain embodiments of the present invention, may be formed from a synthetic biocompatible material, a biological material, or combinations thereof. In accordance with certain embodiments of the present invention, for example, the nanofiber fabric layer(s) may be formed from poly(lactic acid) (PLA), poly(L-lactic acid) (PLLA), poly(lactic-co-glycolic acid) copolymer (PLGA), polycaprolactone (PCL), polyethylene oxide (PEO), collagen, peptides, proteins, nucleic acids, fatty acids, gelatin, chitosan, hyaluronic acid, or combinations thereof.

The embedded cell layer(s), according to certain embodiments of the present invention, may comprise stem cells. In accordance with certain embodiments of the present invention, for example, the embedded cell layer(s) may comprise mammalian (e.g., human) mesenchymal stem cells (MSCs) as referenced above. Because, according to certain embodiments, the therapeutic sleeve device is immunoprivileged, any cell type (e.g., autologous, allogeneic, xenogeneic) may be deployed in the device.

In accordance with certain embodiments of the present invention, the therapeutic sleeve device may further comprise coatings of other advantageous agents (e.g., adhesion molecules, antithrombotic materials, controlled release polymers, agent-releasing materials). In this regard, for example, the nanofiber fabric layer(s) may have an additional coating of adhesion molecules (e.g., fibronectin, fibrinogen, laminins, collagen, vitronectin, proteoglycans, arginyl-glycyl-aspartic (RGD) acid peptides, anti-CD29 cell specific antibody). In this regard, modifying the surface of the nanofiber fabric layer(s) by linking adhesion molecules as referenced above to the nanofiber fabric layer(s) may improve cell adhesion to the therapeutic sleeve device. In accordance with certain embodiments, for example, the nanofiber fabric layer(s) may have an additional coating of antithrombotic materials (e.g., anticoagulants, anti-platelet agents) as referenced above. In this regard, modifying the surface of the nanofiber fabric layer(s) by incorporating anticoagulants (e.g., heparin, enoxaparin, acenocoumarol, fondaparinux, bemiparin, bivalirudin, dalteparin, epoprostenol, tinzaparin, menadiol sodium phosphate, danaparoid, dabigatran etexilate mesilate, rivaroxaban, or warfarin) and/or anti-platelet agents (e.g., acetylsalicylic acid, triflusal, clopidogrel, prasugrel, ticagrelor, ticlopidine, cilostazol, vorapaxar, abciximab, eptifibatide, tirofiban, dipyridamole, picotamide, naproxen, terutroban) may reduce the risk of thrombus formation after implantation of a stent wrapped in a therapeutic sleeve device. In accordance with certain embodiments, for example, the nanofiber fabric layer(s) may have an additional coating of controlled release polymers or other agent-releasing materials (e.g., materials releasing agents such as drugs, proteins, growth factors, exosomes, nucleic acids, cell nutrients, anticoagulants, anti-platelet agents, anti-inflammatory agents) as referenced above. In this regard, modifying the nanofiber fabric layer(s) by incorporating controlled release polymers and other agent-releasing materials may provide materials necessary for cell survival and efficacy of the therapeutic sleeve device. In this regard, certain embodiments of the present invention may improve the efficacy of the therapeutic sleeve device by improving cell adhesion to nanofiber fabric layer(s) and facilitating the release of agents necessary for cell survival. Furthermore, certain embodiments of the present invention may reduce health risks of the therapeutic sleeve device by reducing the thrombogenicity of the therapeutic sleeve device. As such, certain embodiments of the present invention provide better conditions for local growth factor production by stem cells embedded in the nanofiber fabric than traditional stents used to prevent cell proliferation and scar tissue formation; nanofiber covered stents utilized for bypass graft interventions, peripheral interventions, and sealing off aneurysms and iatrogenic vessel perforations; stents with stem cells used to accelerate endothelialization of the stent; or stem cell injections for cardiac tissue regeneration leading to stem cell dilution, washout, and immune attack.

For example, FIG. 1 illustrates a schematic overview of the therapeutic sleeve device according to certain embodiments of the present invention. As shown in FIG. 1, sleeve device 1 illustrated in FIG. 1 includes layers of nanofiber fabric 30 and a layer of stem cells 40 embedded between the layers of nanofiber fabric 30. In this particular embodiment, the sleeve device 1 comprises two layers of nanofiber fabric 30. As shown in FIG. 1, the stem cells 40 embedded in the layers of nanofiber sleeve 30 emit growth factors 20 in the space contained by the vessel wall 50. In this particular embodiment, the sleeve device 1 is wrapped around a stent 10.

Figure 2:
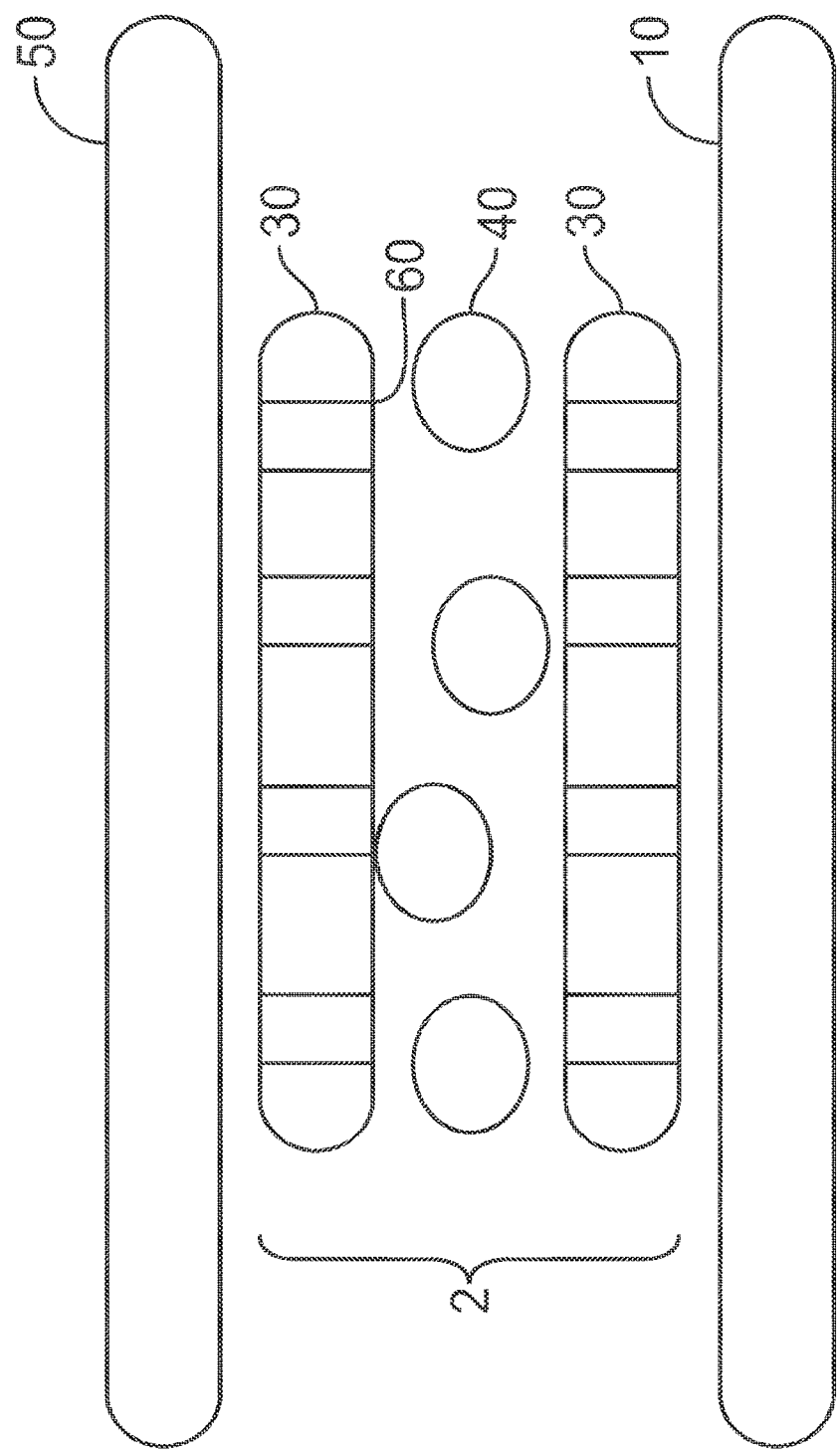
FIG. 2 illustrates a cross section of the therapeutic sleeve device attached to a medical instrument according to certain embodiments of the present invention.

FIG. 2, for example, illustrates a cross-section of the therapeutic sleeve device according to certain embodiments of the present invention. As shown in FIG. 2, the nanofiber fabric assembly 2 illustrated in FIG. 2 includes layers of nanofiber fabric 30 and a layer of stem cells 40 embedded between the layers of nanofiber fabric 30 within the nanofiber fabric assembly 2. In this particular embodiment, the nanofiber fabric assembly 2 comprises two layers of nanofiber fabric 30. FIG. 2 further illustrates that the nanofiber fabric 30 defines a plurality of pores 60. These pores 60 have a greater diameter than that of the embedded cells 40. As shown in FIG. 2, the nanofiber fabric assembly 2 is housed within the vessel wall 50. The nanofiber fabric assembly 2 is further wrapped around a stent 10.

As referenced above, the therapeutic sleeve device illustrated in FIGS. 1 and 2 acts as a platform tailored to the evolving needs of healing and the intravascular production of pro-healing growth factors directly at, near, or distant from damaged tissue.

Figure 3:
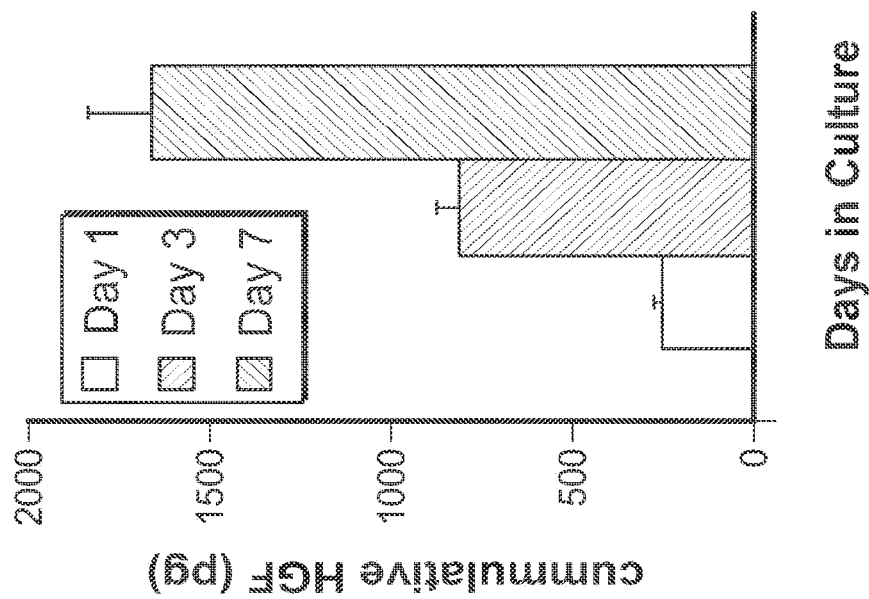
FIG. 3 illustrates that human mesenchymal stem cells on $1 \times 1$ cm$^2$ PLGA nanofiber therapeutic sleeve devices secrete VEGF and HGF over time.
Figure 3:
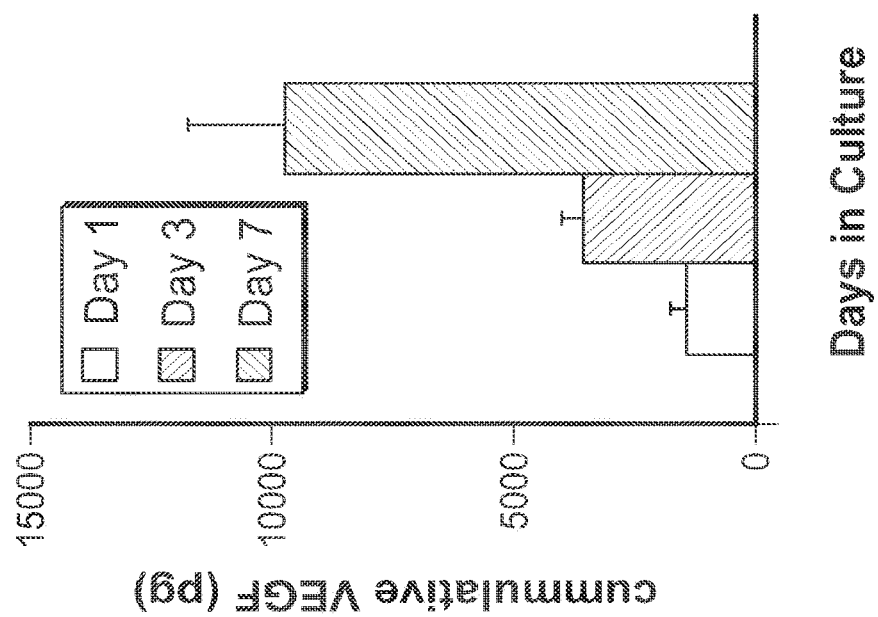

FIG. 3, for example, illustrates the efficacy of the therapeutic sleeve device in promoting intravascular production of vascular endothelial growth factor (VEGF) and hepatocyte growth factor (HGF) by mammalian (e.g., human) mesenchymal stem cells on 1×1 $cm^2$ PLGA nanofiber sleeves over a period of 7 days in culture. In FIG. 3, VEGF production is plotted on the left, while HGF production is plotted on the right. In this regard, FIG. 3 illustrates that the cells embedded in the therapeutic sleeve device successfully produce pro-healing paracrine factors.

Figure 4:
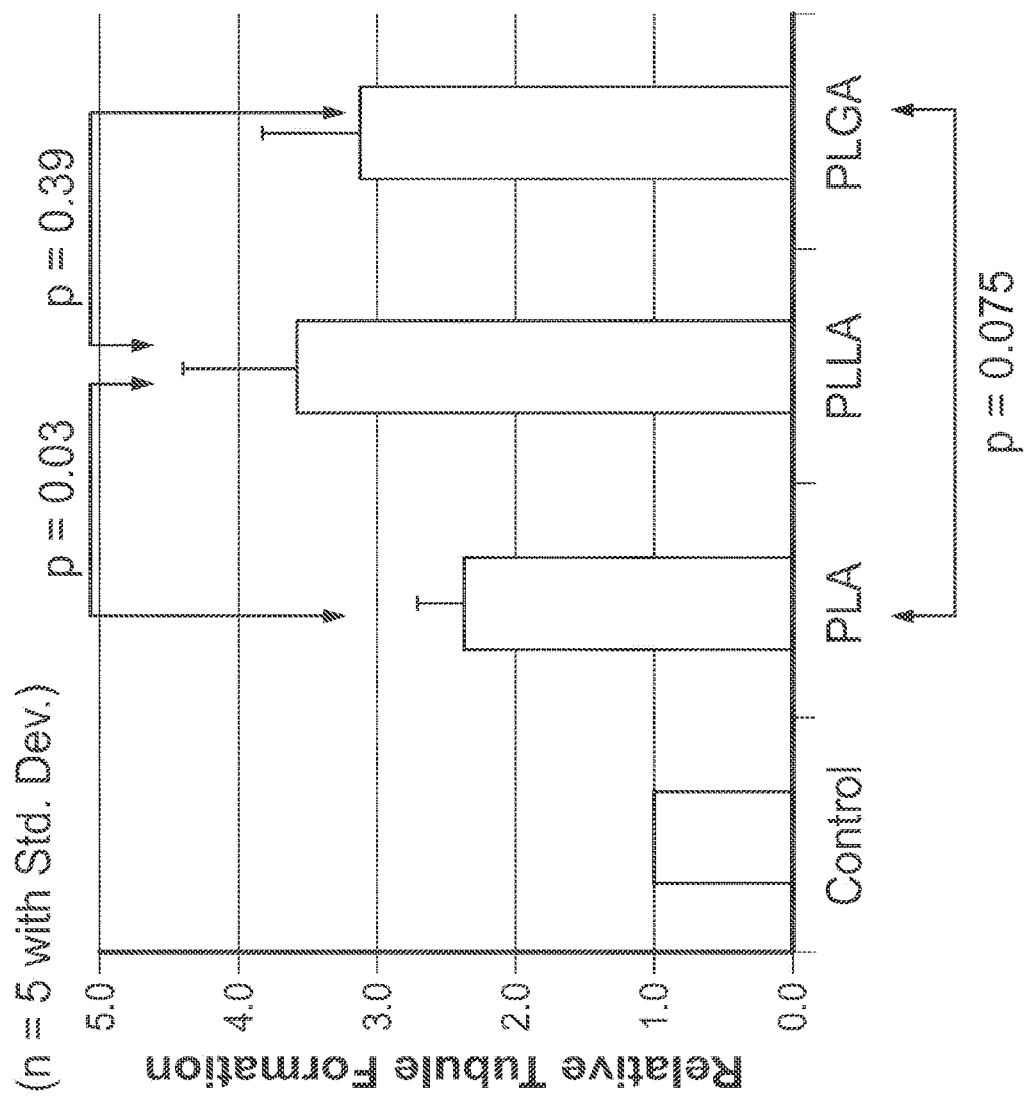
FIG. 4 illustrates that therapeutic sleeve devices fabricated from PLA, PLLA, PLGA and seeded with human mesenchymal stem cells induces greater tubule formation in an in vitro endothelial cell tubule formation assay as compared to a negative control.

FIG. 4 further illustrates the efficacy of the therapeutic sleeve device in promoting production of pro-healing growth factors and healing injured tissue. According to FIG. 4, sufficient growth factors were produced on stem cell-seeded nanofiber sleeves fabricated from PLA, PLLA, and PLGA to better induce randomly seeded human vascular endothelial cells to self-organize into tubules in an in vitro assay as compared to a negative control. As such, the results illustrated in FIG. 4 indicate that angiogenesis has occurred.

Figure 5A:
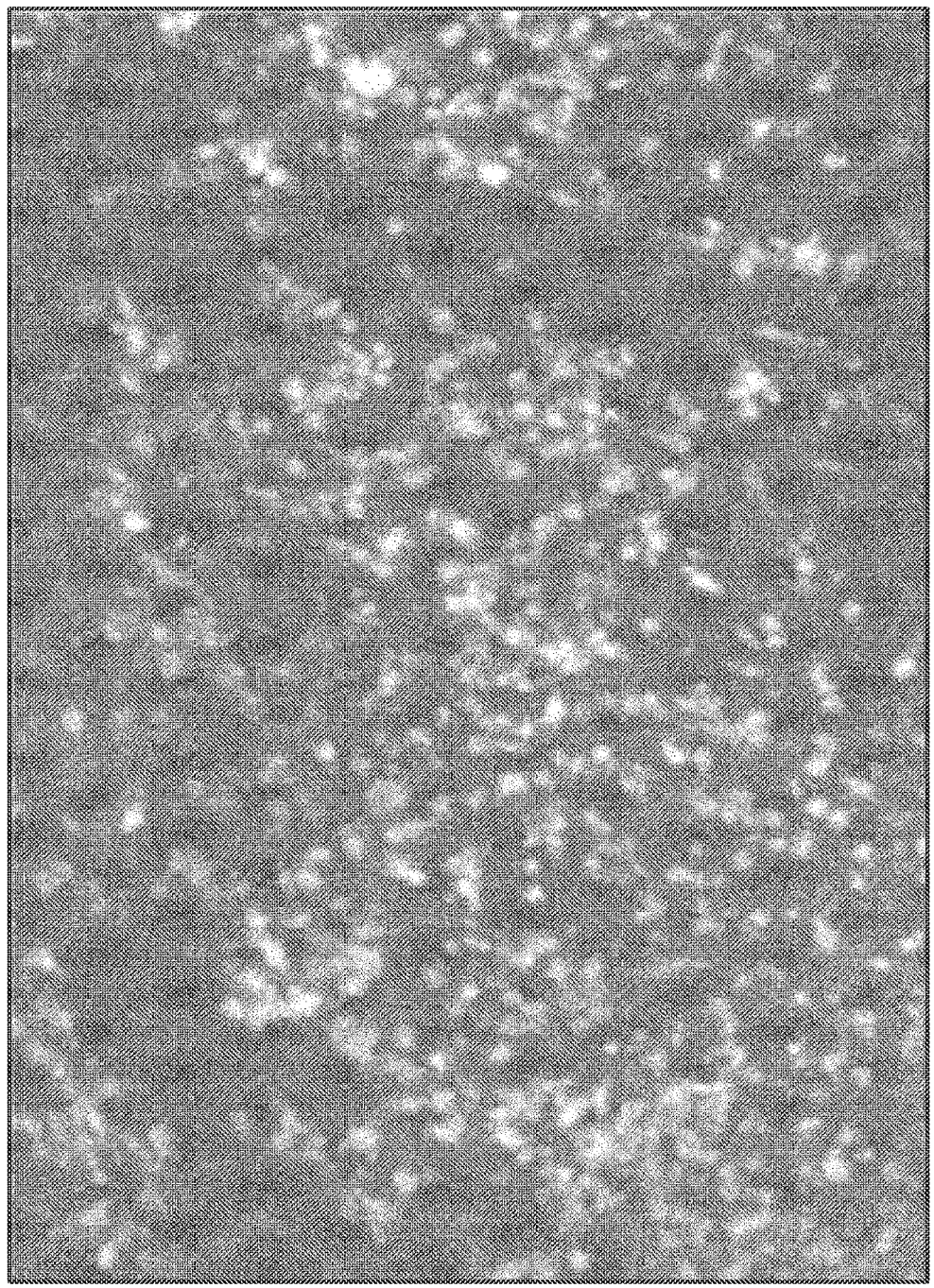
FIG. 5A illustrates higher cell density and nearly 100% stem cell viability on a therapeutic sleeve device coated with fibronectin after 11 days in culture as determined using a calcein AM/ethidium homodimer assay.
Figure 5B:
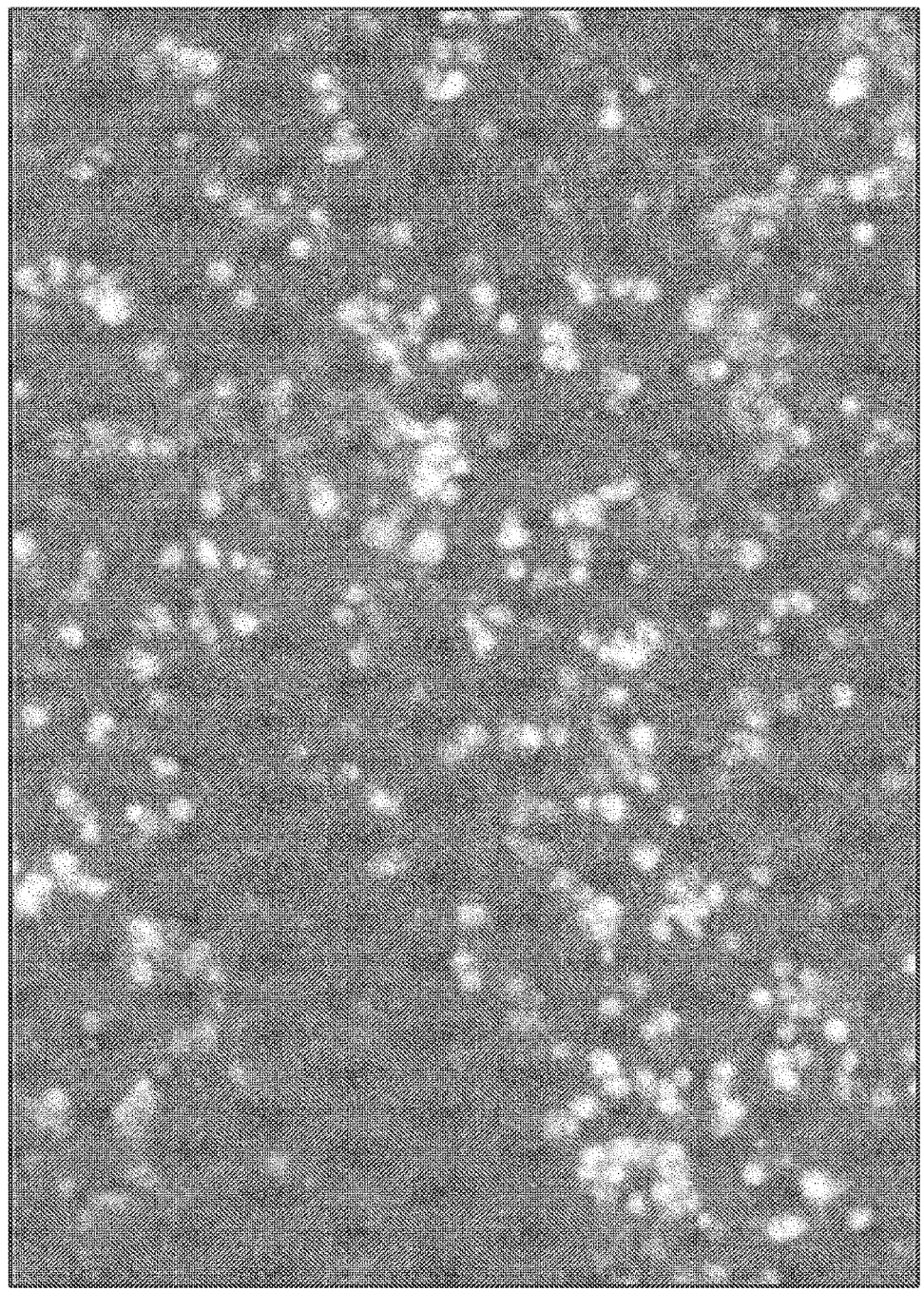
FIG. 5B illustrates a lower cell density and less stem cell viability on a therapeutic sleeve device without a fibronectin coating after 11 days in culture as determined using a calcein AM/ethidium homodimer assay.

As referenced above, in accordance with certain embodiments of the present invention, the therapeutic sleeve device may comprise adhesion molecules to improve stem cell adhesion to the nanofiber sleeve. In such embodiments, surface modification of nanofiber fabric via linking to adhesion molecules (e.g., fibronectin, fibrinogen, laminins, collagen, vitronectin, proteoglycans, arginyl-glycyl-aspartic (RGD) acid peptides, anti-CD29 cell specific antibody) may be used to improve adhesion of cells to the nanofiber sleeve. Surface modification may be performed before or after attaching the therapeutic sleeve device to a stent. In one embodiment, a surface-modified therapeutic sleeve device was formed by direct electrospinning and then placed in a solution of 25 µg/mL of fibronectin in an incubator at 37 deg C. for 2 hours prior to embedding with stem cells. FIGS. 5A and 5B illustrate the viability of mammalian (e.g., porcine) mesenchymal stem cells on a therapeutic sleeve device with and without adhesion molecules (e.g., fibronectin) after 11 days in culture as determined using a calcein AM/ethidium homodimer assay. Viable cells (bright white) in both FIGS. 5A and 5B greatly outnumber nonviable cells (dim gray). However, as illustrated in FIGS. 5A and 5B, incorporation of fibronectin into the therapeutic sleeve device in FIG. 5A improved stem cell adhesion density and long term stem cell viability as compared to the therapeutic sleeve device without a fibronectin coating in FIG. 5B.

Figure 6:
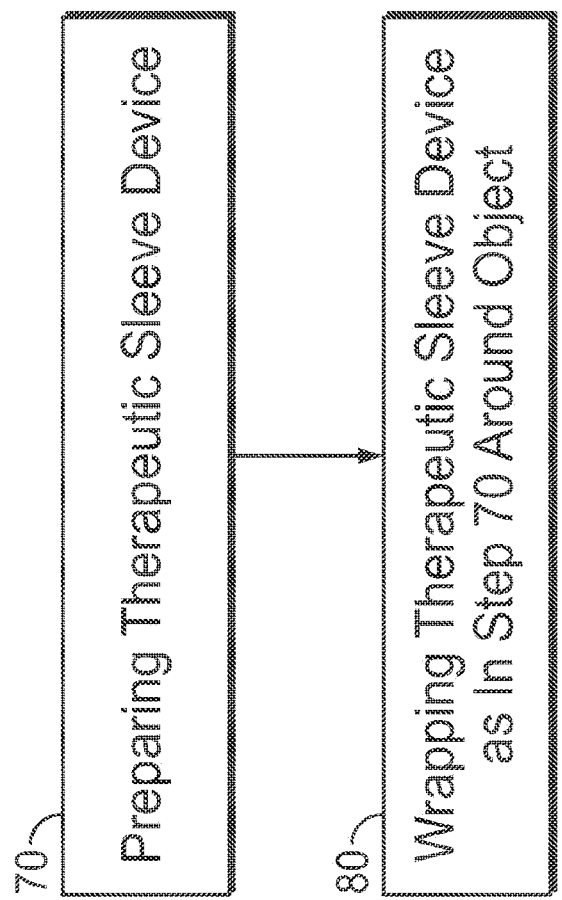
FIG. 6 illustrates a method of treatment using the therapeutic sleeve device according to certain embodiments of the present invention.

In another aspect illustrated in FIG. 6, the present invention provides methods of using therapeutic sleeve devices according to certain embodiments of the present invention. For example, therapeutic sleeve devices according to certain embodiments of the present invention can be used in conjunction with many medical instruments, including, but not limited to, stents, pacemakers, implantable cardioverter-defibrillators, pacemaker leads, implantable cardioverter-defibrillator leads, biventricular implantable cardioverter-defibrillator leads, artificial hearts, artificial valves, ventricular assist devices, balloon pumps, catheters, central venous lines, orthopedic implants, other implants, wound healing packing, and wound healing gauze. According to certain embodiments of the present invention, therapeutic sleeve devices are used in conjunction with stents. Stents, according to certain embodiments, may comprise bare metal stents, drug-eluting stents, stent grafts, or biodegradable scaffolds. However, in certain embodiments according to the present invention, the therapeutic sleeve device may be used without a medical instrument. For example, in some embodiments, the therapeutic sleeve device may be wrapped directly around any tissues, muscles, organs, or blood vessels, including bypass grafts.

According to certain embodiments of the present invention, to wrap therapeutic sleeve devices around stents, one of several attachment methods may be used. In certain embodiments, therapeutic sleeve devices may be attached to stents via direct electrospinning. For direct electrospinning, a therapeutic sleeve device can be formed directly on a stent via electrospinning. To form a therapeutic sleeve device directly on a stent, an unexpanded, partially expanded, or fully expanded stent is mounted along the axis of a shaft rotating at approximately 100 rpm. A wire, connected to a power source, is placed inside the lumen of an expanded stent or a stent delivery balloon for an unexpanded stent, and the stent is rotated. Nanofiber materials (e.g., PLA, PLLA, PLGA, etc.) at a concentration of 7.5 wt % in dichloromethane solvent can be loaded into a syringe pump and, through an 18G blunt-tipped needle connected to a power source, drawn out to the rotating stent by a voltage potential. Electrospinning settings may comprise a voltage potential of 10-20 kV, a blunt-tipped needle to stent distance of 6-12 cm, a syringe pump infusion rate of 1.5-5.0 mL/hr, and an electrospinning time of 5-15 min, but these settings can be changed depending on such factors as desired nanofiber sleeve thickness, stent size, source polymer concentration, or desired nanofiber pore sizes. In accordance with certain embodiments, multiple nanofiber fabric layer(s) can be made by repeating the electrospinning process.

In certain embodiments, therapeutic sleeve devices may be attached to stents via microsuturing. For microsuturing, a therapeutic sleeve device can be attached to a stent using a micro-suture (e.g., 7-0 Prolene) or any suitable biocompatible adhesive. Nanofiber fabric layer(s) can be attached to the inner, outer, or both aspects of the stent and can cover the stent partially or entirely. In accordance with certain embodiments, multiple nanofiber fabric layer(s) may be attached on one stent. Once attached to the therapeutic sleeve device, the stent can be crimped onto a delivery balloon for implantation.

In certain embodiments, therapeutic sleeve devices may be attached to stents via stent sandwiching. For stent sandwiching, a therapeutic sleeve device can be physically secured or left unattached to a stent. A second stent can then be crimped concentrically around the first stent, sandwiching the therapeutic sleeve device between the two stents. In accordance with certain embodiments, the sandwiching stent may completely or partially overlap the first stent (i.e., the sandwiching stent may be the same length, longer, or shorter than the first stent). In certain embodiments, multiple nanofiber fabric layer(s) can be sandwiched as such between two stents and, analogously, multiple stent layers may be used. The primary advantage to stent sandwiching is that it yields a more robust sleeve that can be useful in more mechanically demanding environments.

According to certain embodiments of the present invention, cells can be embedded into nanofiber fabric layer(s) before attaching the therapeutic sleeve device to a stent or after attaching the nanofiber fabric layer(s) to a stent. According to certain embodiments, to embed cells in nanofiber fabric layer(s), one of several methods may be used. In certain embodiments, stem cells may be embedded in nanofiber fabric layer(s) utilizing pre-incubation embedding. For pre-incubation embedding in certain embodiments, stem cells can be cultured in standard tissue culture flasks using methods known to one of ordinary skill in the art. Once confluent, the stem cells can be harvested from the tissue culture flasks using 0.25% trypsin and reconcentrated in media to a concentration of at least $10^5$ cells/mL. In certain embodiments, lower cell concentrations may be used. Unattached nanofiber fabric layer(s) can be immersed in the concentrated stem cell suspension and placed in an incubator for at least 30 min. According to certain embodiments, the unattached nanofiber fabric layer(s) can be placed in the incubator for up to 6 hours or more to improve cell adhesion.

In certain embodiments, cells can be embedded into nanofiber fabric layer(s) already attached to a stent. According to certain embodiments, stem cells may be embedded in nanofiber fabric layer(s) using post-incubation embedding. As such, in some embodiments, the nanofiber fabric layer(s) attached to a stent can be immersed in a concentrated suspension of stem cells and placed in a tissue culture incubator for at least 30 minutes, where the stent can be rotated approximately every 5-10 min. According to certain embodiments, the nanofiber fabric layer(s) attached to a stent may be incubated up to 6 hours or longer to improve cell adhesion. In certain embodiments, lower cell concentrations may be used.

In certain embodiments, cells may be embedded in nanofiber fabric layer(s) using in-situ embedding. According to certain embodiments, stem cells can be incorporated directly into the nanofiber fabric layer(s) during the electrospinning process. According to one embodiment, stem cells in a concentrated suspension (i.e., at least $10^5$ cells/mL) can be dripped using a syringe pump, nebulized using commercial nebulizer systems, or microsprayed using cell microsprayers (e.g., Penn-Century™ MicroSprayer® Aerosolizer) directly onto the rotating electrospinning target. Alternatively, in another embodiment, the rotating electrospinning target can be partially immersed in a concentrated suspension of cells that may be continually agitated.

As illustrated in FIG. 6, the first step 70 is for the therapeutic sleeve device having the characteristics discussed above to be prepared. In the second step 80, the therapeutic sleeve device may be wrapped around an object. In this regard, the therapeutic sleeve device will provide a subject in need thereof with beneficial tissue healing effects provided by the stem cells embedded in the pores of the device without any adverse effects in the current commercial applications of stem cells referenced above, including cell dilution, washout, and immune attack.

As previously discussed, certain embodiments according to the present invention utilize the method illustrated in FIG. 6 with an object comprising a tissue, an organ or a portion of an organ, a blood vessel, or a bypass graft. Furthermore, in certain embodiments the object may comprise a medical instrument. The medical instrument may comprise stents, pacemakers, implantable cardioverter-defibrillators, pacemaker leads, implantable cardioverter-defibrillator leads, biventricular implantable cardioverter-defibrillator leads, artificial hearts, artificial valves, ventricular assist devices, balloon pumps, catheters, central venous lines, orthopedic implants, wound healing packing, or wound healing gauze. According to certain embodiments, the medical instrument comprises a stent. In such embodiments, the stent may be employed in coronary, peripheral, venous, or non-vascular uses. The stent used in such embodiments may comprise a bare metal stent, a drug-eluting stent, a stent graft, or a biodegradable stent.

As previously discussed, certain embodiments according to the present invention provide sleeve devices suitable for a wide range of therapeutic uses. In accordance with certain embodiments, the therapeutic sleeve device includes a nonwoven fiber fabric assembly, which defines a plurality of pores, and a plurality of cells embedded in the nonwoven fiber fabric assembly. Furthermore, the nonwoven fiber fabric assembly comprises a first nonwoven fiber fabric layer and a second nonwoven fiber fabric layer, and the embedded cells are embedded between these two nonwoven fiber fabric layers. In certain embodiments, the nonwoven fiber fabric assembly may comprise a nanofiber fabric assembly. Optionally, the embedded cells may be stem cells, specifically mesenchymal stem cells. The therapeutic sleeve device as described the embedded cells to produce and release paracrine factors. Within the therapeutic sleeve device, the pores defined by the nonwoven fiber fabric assay have a smaller pore size than the embedded cells and any foreign host cells (e.g., host immune cells) but a larger pore size than any products, nutrients, and wastes produced or required by the embedded cells. For example, to embed cells of diameters of about 20 microns producing growth factors of diameters less than 100 nanometers, the pore diameter may be less than about 15-20 microns and greater than about 100 nanometers. Additionally, to allow entry and exit of exosomes, which have diameters less than 300 nanometers, the pore diameter may be greater than 300 nanometers.

According to certain embodiments of the present invention, the nonwoven fiber fabric assembly may comprise at least one biodegradable material, non-biodegradable material, bioabsorbable material, or non-bioabsorbable material. The nonwoven fiber fabric assembly may comprise at least one synthetic material, biological material, or any combination thereof. Thus, the nanofiber fabric assembly may comprise at least one of poly(lactic acid), poly(L-lactic acid), poly(lactic-co-glycolic acid) copolymer, polycaprolactone, or polyethylene terephthalate, or, alternatively, at least one of collagen, peptides, proteins, nucleic acids, fatty acids, gelatin, chitosan, or hyaluronic acid. The therapeutic sleeve device may also optionally comprise at least one layer of adhesion molecules. These adhesion molecules can be at least one of fibronectin, fibrinogen, laminins, collagen, vitronectin, proteoglycans, arginyl-glycyl-aspartic (RGD) acid peptides, or cell specific antibodies (e.g., anti-CD29 antibody). The therapeutic sleeve device may further optionally comprise at least one layer of antithrombotic material. These antithrombotic materials can be anticoagulants, anti-platelet agents, or a combination thereof. Specifically, the antithrombotic materials may comprise any combination of heparin, enoxaparin, or eptifibatide. The therapeutic sleeve device may further optionally comprise at least one layer of controlled release polymers and/or agent-releasing materials, wherein the released agents may comprise drugs, proteins, growth factors, cell nutrients, anticoagulants, anti-platelet agents, or anti-inflammatory drugs.

Some embodiments of the present invention include a nonwoven fiber fabric assembly with embedded stem cells wrapped around a medical instrument, which provides a platform from which stem cells can be placed directly at or so that it can release factors to injured tissue, while also being shielded from dilution, washout, and immune attack, in order to provide continuous production of pro-healing paracrine factors.

EXAMPLES

The present disclosure is further illustrated by the following examples, which in no way should be construed as being limiting. That is, the specific features described in the following examples are merely illustrative, and not limiting.

Fabrication of Nanofiber Sleeve

Nanofiber stent sleeves are electrospun onto the external surfaces of non-medicated cobalt chromium stents (Medtronic, Minneapolis, Minn.). Poly (L-lactide/glycolide) co-polymer (PLG 8531; Purac, Inc., Lincolnshire, Ill.) was dissolved in a mixture dichloromethane and methanol (7:3 vol:vol). The stents were balloon-expanded to their nominal diameters and removed from the balloon. The co-polymer was then electrospun onto the stent at 12 kV (Gamma Model ES30P-5W/DAM; Gamma High Voltage Research, Ormond Beach, Fla.) with a flow rate of 3.5 mL/hr via an 22G×1.5 inch blunt-tip needle at a distance of 9 cm from the collecting target for 25 minutes using a syringe pump (NE-300 Just Infusion™ Syringe Pump; New Era Pump Systems, Farmingdale, N.Y.). To produce a uniform nanofiber sleeve thickness, the stent was continuously rotated along its longitudinal axis during electrospinning at 130 revolutions per minute. The completed electrospun nanofiber stents were sterilized in a solution of 70% EtOH over 12 hours. Nanofiber sleeve morphology was then imaged using a Hitachi S4700 scanning electron microscope (SEM) both at baseline and after crimping onto a 2.5×12 mm angioplasty balloon (Medtronic, Minneapolis, Minn.) using a radial compression stent crimper (Model RMC, Blockwise Engineering, Phoenix, Ariz.) and re-expanding to nominal diameter.

The electrospun nanofiber stent sleeves consist of randomly oriented fibers which uniformly covered the stent with the typical physical pore size less than 10 um in diameter. The tortuosity of the pathway through the mesh further reduces the effective pore diameter. Crimping the stent onto an angioplasty balloon followed by balloon re-expansion, as would be required for clinical implantation of the device, did not significantly affect nanofiber sleeve architecture or geometry, although the individual fibers showed evidence of stretching without structural failure. The nanofiber sleeve remained securely on the stent after passing through a clinical grade 8 Fr guide catheter. The fibrous architecture of the nanofiber sleeve can be slightly varied by modulating the electrospinning conditions to produce different pore sizes or fiber orientations. Increasing electrospinning voltages from 12 kV to 18 kV, for instance, tended to result in a denser architecture, with qualitatively more organized fiber orientations and overall slightly smaller pore sizes.

Nanofiber Sleeve Impregnation, Overcoating, Cell Coverage, and Cell Viability

Nanofiber Sleeve Impregnation and Overcoating: Pig mesenchymal stem cells (pMSCs) were isolated and expanded from bone marrow biopsies of Yorkshire farm pigs. For nanofiber impregnation, pMSCs at passages 4-6 were harvested using 0.25% Trypsin-EDTA (Gibco), and re-suspended in culture medium at a concentration of $3\times10^6$ pMSCs/mL. Nanofiber stent sleeves were then immersed in the pMSC suspension in a 1.5 mL Eppendorf tube which was gently rotated for 30 minutes at 37° C. to ensure uniform cell adhesion. Excess non-adherent stem cells were washed off with fresh medium. The cell-impregnated nanofiber stent sleeves were then incubated in cell culture medium for an additional 24 hours prior to use. The cell-impregnated nanofiber sleeves were cultured for 7 days prior to over-coating them with an additional layer of nanofiber. On Day 8, the sleeves were electrospun under sterile conditions with another layer of nanofiber for 12 min, and cultured for another 6 days prior to use.

Cell Coverage and Viability: Cell coverage and stem cell viability on the nanofiber stent sleeve were evaluated on days 1 and 8 after cell impregnation using a Calcein-AM/Ethidium homodimer assay (LIVE/DEAD® Viability Assay, Life Technologies; Carlsbad, Calif.). Briefly, cell-impregnated nanofiber stent sleeves were incubated in 2 µM Calcein-AM and 4 µM Ethidium homodimer solution for 30 minutes. The nanofiber stent sleeves were briefly washed in phosphate buffered saline and then imaged using confocal fluorescence microscopy (Zeiss Axio Observer with 710 NLO-Meta confocal module; Jena, Germany).

Pig mesenchymal stem cells retained high viability after being embedded into the nanofiber stent sleeve. On day 1 after seeding, stem cell coverage of the sleeve was initially sparse, but the cells continued to multiply on the sleeve, and became nearly confluent on day 8. The mesenchymal stem cells appeared healthy and maintained their natural elongated morphologies. Control sleeves had no cells. Cell embedding and viability were poor for those cells immediately over the stent wire, possibly reflecting stent wire impediment of efficient nutrient and waste transfer. Overcoating cell-impregnated sleeves after 7 days with an additional layer of nanofiber resulted in an initial steep drop in the number of viable cells in the sleeve, but after 6 additional days in culture post-overcoating, confluence was regained with again greater than 90% viability.

Flow Cytometry

To confirm that the nanofiber sleeve does not induce differentiation of contained cells, pMSCs were collected and analyzed for expression of MSC-specific surface markers by flow cytometry seven days after incorporation in the nanofiber sleeve. Cells were analyzed for CD90, CD44, and CD34 expressions using commercial staining kits (BD Bioscience) per manufacturer guidelines and samples were analyzed using FACS LSR-II (BD Bioscience). Data were gated, analyzed, and compensated using FlowJo software (Tree Star, Ashland Oreg.). 7AAD-stained nonviable cells and cell aggregates were excluded during the analysis. To reliably distinguish positive and negative staining populations, standard isotype controls (BD Bioscience) were used as negative controls.

Flow cytometry analysis showed that pig mesenchymal stem cells embedded in the nanofiber stent sleeve retained cell surface markers expressed by stem cells after 7 days. Patterns of cell surface marker expression of CD90, CD44, and CD34 were identical between pMSCs grown in culture de novo and those embedded within the nanofiber sleeve. The materials and fibrous structure of the nanofiber stent sleeve therefore do not induce differentiation of embedded MSCs.

Paracrine Factor Production and In Vitro Angiogenesis

Paracrine Factor Production: Human MSCs (hMSCs) were obtained from Lonza (Walkersville, Md.) and expanded. The hMSCs were embedded into 1×1 cm$^2$ nanofiber stent sleeve patches by incubating the sleeves in a 0.5 mL solution of 2×10$^5$ hMSCs (passage number 6) for 90 minutes, and then washing off the excess unattached hMSCs. Conditioned media was collected 1, 3, and 7 days after stem cell embedding. Secreted vascular endothelial growth factor (VEGF) and hepatocyte growth factor (HGF) were analyzed using enzyme linked immunosorbent assays (Quantikine® ELISA kits, R&D Systems; Minneapolis, Minn.).

In Vitro Angiogenesis: For the Human Umbilical Vein Endothelial Cell (HUVEC) tubule formation assay, 6-well plates were coated with 250 µl of Geltrex® (Invitrogen) and seeded with 1.8×10$^5$ HUVECs suspended in 2.5 ml of Medium 200PRF (Invitrogen). A 1×1 cm$^2$ nanofiber sleeve seeded with hMSCs and incubated for 7 days was placed in each well. Controls consisted of a 1×1 cm$^2$ nanofiber sleeve without hMSCs. At 18 hours, images of the tubule network were obtained, and the lengths of the tubules were measured using ImageJ software (Bethesda, Md.). The lengths of the tubules in the experimental wells were normalized to the average length in the control wells.

Human MSCs (hMSCs) embedded within nanofiber sleeves produce growth factors relevant to angiogenesis and myocardial repair. 1×1 cm$^2$ nanofiber sleeve patches seeded with a 0.5 mL solution of 2×10$^5$ hMSCs continued to produce vascular endothelial growth factor (VEGF) and hepatocyte growth factor (HGF) over 7 days in culture. The daily rate of growth factor production remained substantially unchanged from day 1 to day 7. Control nanofiber sleeves without hMSCs incubated in culture media alone yielded negligible amounts of growth factor. HUVECs exposed to nanofiber sleeves with embedded hMSCs spontaneously organized into tubules to a 3.1±0.7 fold greater extent than did HUVECs exposed to control sleeve patches without cells (p=0.003). These data suggest that the embedded MSCs retain not only "stemness" but the ability to produce relevant paracrine factors as well. Most importantly, the ability to induce angiogenic tubule formation shows that the biological function of the paracrine factors secreted by the MSCs is maintained.

Endovascular Implantation in Swine Model

Nanofiber sleeves were electrospun onto balloon-expanded non-medicated cobalt chromium bare metal stents (Medtronic, Minneapolis, Minn.), crimped back down onto its stent delivery balloon (Medtronic, Minneapolis, Minn.) using a radial compression stent crimper (Model RMC, Blockwise Engineering, Phoenix, Ariz.), and seeded with pMSCs. Via an 8-French Judkins Right 4 (JR4) Vista Brite Tip® guiding catheter (Cordis, Bridgewater, N.J.), the stent was delivered over a 180 cm Luge™ wire (Boston Scientific, Natick, Mass.) to the mid-segment of the pig left umbilical artery where it was deployed at 9 atm and post-dilated to 12 atm to ensure vessel wall apposition. The pig was treated with aspirin 324 mg, clopidogrel 600 mg, and intravenous unfractionated heparin 5000U pre-procedure, and received daily aspirin 81 mg and clopidogrel 75 mg post-procedure. The angiographic appearance of the umbilical artery was obtained using manual injection of iodinated contrast (Omnipaque™, GE Healthcare, Princeton, N.J.) immediately pre-procedure, during stent inflation, and at 60 minutes and 7 days post-implantation.

Nanofiber stent sleeves were successfully delivered using standard clinical vascular guidewires and guide catheters to the mid segment of the left umbilical artery of young Yorkshire swine. The angiographic appearance of the left umbilical artery pre-implantation was recorded, and the nanofiber stent sleeve was deployed in the mid left umbilical artery with vessel occlusion during balloon inflation confirming stent apposition. There were no peri-procedural complications, and no adverse events were observed up to 1 week after implantation. A daily regimen of aspirin 81 mg and clopidogrel 75 mg was tolerated without any adverse effect. The angiographic appearance of the artery at 60 minutes and at 7 days after implantation was not substantially different from its appearance pre-implantation. Normal flow was preserved.

These and other modifications and variations to the present invention may be practiced by those of ordinary skill in the art without departing from the spirit and scope of the present invention, which is more particularly set forth in the appended claims. In addition, it should be understood that aspects of the various embodiments may be interchanged in whole or in part. Furthermore, those of ordinary skill in the art will appreciate that the foregoing description is by way of example only, and it is not intended to limit the invention as further described in such appended claims. Therefore, the spirit and scope of the appended claims should not be limited to the exemplary description of the versions contained herein.

What is claimed is:

1. A method of treating a subject in need thereof, comprising:
   (a) preparing a therapeutic sleeve device comprising:
      i. a nonwoven fiber fabric assembly defining a plurality of pores, wherein said nonwoven fiber fabric assembly comprises a nanofiber fabric assembly comprising at least one of poly(lactic acid), poly(L-lactic acid), poly(lactic-co-glycolic acid) copolymer, polycaprolactone, or polyethylene terephthalate; and
      ii. a plurality of stem cells, each stem cell of the plurality of stem cells embedded in one of the plurality of pores of the nonwoven fiber fabric assembly, wherein each stem cell of the plurality of stem cells is configured to emit paracrine factors, the paracrine factors being configured to promote healing of a tissue, organ, or wound of the subject,
      each stem cell of the plurality of stem cells has a cell diameter, wherein each pore of the plurality of pores has a maximal pore size of less than 10 microns in diameter,
      the maximal pore size of each pore is less than the cell diameter to form a cage inside which any of the plurality of stem cells is embedded and retained thereby configuring the cage to prevent interaction between cells of the subject and the plurality of stem cells in response to the therapeutic sleeve device being inserted into the subject, and
      the maximal pore size is larger than a diameter of the paracrine factors emitted by each stem cell of the plurality of stem cells to allow for the paracrine factors to be emitted through the cage while the cage prevents washout and dilution of the plurality of stem cells from the therapeutic sleeve;
   (b) wrapping the therapeutic sleeve device around an object, wherein the object comprises a medical instrument, a tissue, an organ or a portion of an organ, a blood vessel, or a bypass graft, and
   (c) implanting the wrapped object into the subject,
   wherein the therapeutic sleeve device prevents embedded stem cells from dilution and washout, and protects them from the immune system of the subject.

2. The method of treatment according to claim 1, wherein the medical instrument comprises stents, pacemakers, implantable cardioverter-defibrillators, pacemaker leads, implantable cardioverter-defibrillator leads, biventricular implantable cardioverter-defibrillator leads, artificial hearts, artificial valves, ventricular assist devices, balloon pumps, catheters, central venous lines, orthopedic implants, wound healing packing, or wound healing gauze.

3. The method of treatment according to claim 1, wherein the medical instrument comprises a stent.

4. The method of treatment according to claim 3, wherein the stent comprises a bare metal stent, a drug-eluting stent, a stent graft, or a biodegradable scaffold.

5. The method of treatment according to claim 1, wherein the nonwoven fiber fabric assembly further comprises a first nonwoven fiber fabric layer and a second nonwoven fiber fabric layer and the plurality of stem cells are embedded between the first nonwoven fiber fabric layer and the second nonwoven fiber fabric layer.

6. The method of treatment according to claim 1, wherein the stem cells are mesenchymal stem cells.

7. The method of treatment according to claim 1, wherein the maximal pore size is less than cell diameters of the cells of the subject.

8. The method of treatment according to claim 7, wherein the cells of the subject comprise host immune cells.

9. The method of treatment according to claim 1, wherein an average pore size is greater than embedded cell product, nutrient, or waste diameters.

10. The method of treatment according to claim 9, wherein the average pore size is greater than about 100 nanometers, the cell diameter is about 20 microns, and paracrine factor diameters are less than 100 nanometers.

11. The method of treatment according to claim 9, wherein the average pore size is greater than about 300 nanometers, the cell diameter is about 20 microns, and exosome diameters are about 300 nanometers.

12. The method of treatment according to claim 1, wherein the nanofiber fabric assembly further comprises at least one of collagen, peptides, proteins, nucleic acids, fatty acids, gelatin, chitosan, or hyaluronic acid.

13. The method of treatment according to claim 1, wherein the therapeutic sleeve device further comprises at least one layer of adhesion molecules.

14. The method of treatment according to claim 13, wherein the adhesion molecules comprise at least one of fibronectin, fibrinogen, laminins, collagen, vitronectin, proteoglycans, arginyl-glycyl-aspartic (RGD) acid peptides, or cell specific antibodies.

15. The method of treatment according to claim 14, wherein the cell specific antibodies comprise anti-CD29 antibody.

16. The method of treatment according to claim 1, wherein the therapeutic sleeve device further comprises at least one layer of an antithrombotic material.

17. The method of treatment according to claim 16, wherein the antithrombotic material comprises at least one of an anticoagulant or an anti-platelet agent.

* * * * *